United States Patent [19]
Bloomfield

[11] Patent Number: 5,829,588
[45] Date of Patent: Nov. 3, 1998

[54] SHARPS CONTAINER

[76] Inventor: Lawrence Michael Bloomfield, 5 Mooloo Court, Shailer Park, Queensland, 4128, Australia

[21] Appl. No.: 716,176

[22] PCT Filed: Mar. 27, 1995

[86] PCT No.: PCT/AU95/00171

§ 371 Date: Sep. 23, 1996

§ 102(e) Date: Sep. 23, 1996

[87] PCT Pub. No.: WO95/26210

PCT Pub. Date: Oct. 5, 1995

[30] Foreign Application Priority Data

Mar. 25, 1994 [AU] Australia ............................... PM 4742
Jan. 9, 1995 [AU] Australia ............................... PN 0403

[51] Int. Cl.$^6$ .................................................. B65D 83/10
[52] U.S. Cl. ........................................... 206/366; 206/1.5
[58] Field of Search .................................... 220/408, 410, 220/395; 206/366, 1.5

[56] References Cited

U.S. PATENT DOCUMENTS

| | | | |
|---|---|---|---|
| 2,710,491 | 6/1955 | Carlson | 220/408 |
| 3,964,630 | 6/1976 | Getz | 220/4 R |
| 4,715,498 | 12/1987 | Hanifl | 206/366 |
| 4,863,052 | 9/1989 | Lambert | 220/1 T |
| 4,972,950 | 11/1990 | Shillington | 206/366 |
| 5,178,322 | 1/1993 | Shillington | 232/44 |

*Primary Examiner*—David T. Fidei
*Assistant Examiner*—Nhan T. Lam
*Attorney, Agent, or Firm*—Young & Thompson

[57] ABSTRACT

A reusable sharps container (10) comprising a hollow outer container body (11), a disposable liner (12) located inside the hollow body, the hollow body having a slidable trap door (shown in phantom in FIG. 1) (13) which can be removed so that the liner (12) can be replaced and the container having a mouth (14) with a co-operating lid (15) connectable to the container or liner so that sharps can pass through the opening (14) and into the liner (12).

17 Claims, 11 Drawing Sheets

SHARPS CONTAINER

TECHNICAL FIELD OF THE INVENTION

THIS INVENTION relates to sharps containers of the reusable and disposable type and in particular but not limited to a reusable sharps container disposable liner combination for use in the disposal of medical sharps including scalpels and hypodermic needles.

BACKGROUND ART

Sharps related accidents occur in a clinical environment. Medical staff have been infected with the HIV virus and the Hepatitis B virus through needle stick injuries.

With a growing concern over needle stick and other sharps related injuries safe systematic disposal of sharps has become a requirement when handling sharps in a clinical situation.

It is now common to use a special container for holding sharps and when the container is full, it is disposed of along with the sharps inside. The benefit of these types of containers is that they are usually designed so that once sealed, the container cannot be reopened. This means that disposal can be carried out without risk to waste disposal staff.

The main disadvantage with these containers is the expense associated with buying a new container once an existing container is full. It is an object of the present invention to alleviate this problem.

OUTLINE OF THE INVENTION

In one aspect, the present invention resides in a reusable sharps container comprising a hollow outer container body and a disposable liner located inside the hollow body to hold sharps, the body having an openable closure means so that the liner can be replaced and a mouth with a co-operating lid so that sharps can pass through the mouth and travel into the liner, the lid being used to close the mouth. The lid can be fitted to the reusable container or to the liner in order to close the mouth. The openable closure means of the container is fitted to the container body below the liner so that when the openable closure means is open, the liner is automatically discharged from the container body.

The container body is preferably moulded or otherwise formed from plastic material, although any suitable material can be employed. The openable closure means is preferably lockable so that unauthorized access is inhibited. The closure means is typically a trap door preferably in the form of a slidable drawer. The closure means can be equipped with a sump. The reusable container is preferably braced at its base to inhibit flexing of the container and to thereby avoid accidental dislodgment of the closure means.

In a preferred form where the lid is secured to the reusable container, the mouth includes a socket means and the lid comprises a plug means which fits into the socket, the lid having release means so that the lid can be released from inside the container body but not from the outside. The lid can have any kind of plug-in retention means including a resistance fit, bayonet type coupling, or the lid can have a clip action release means.

The mouth typically employs a sharps removal means to aid removal of sharps from separately disposable non-sharps. Typically, a notch or other needle gripping means is provided for removing hypodermic needles from syringes.

The container preferably includes a sharps level indicator to give an indication of when it is necessary to change the liner. The level indicator is preferably in the form of a protruding portion or funnel which extends inside the liner or is formed as part of the liner. The protruding portion or funnel typically occupies space that would otherwise be occupied by sharps so that the liner is never full to overflowing. The protruding portion or funnel is typically in the form of a tapered wall depending down from the lid and into the container body and thereby into the liner. The protruding portion or funnel preferably includes a releasable container body attachment means so that the protruding portion or funnel can be removed for cleaning purposes. It is most preferably only operable from the inside.

The liner can be any suitable means for holding the sharps and is typically a disposable hollow plastic or cardboard container having a narrow or wide open mouth alignable with a mouth of the reusable container to thereby form the mouth for entrance of sharps. The liner and container body are preferably so sized and dimensioned that the liner is held upright within the container body in predetermined position relative to the mouth. In a particularly preferred form, the liner is formed from a folded blank of waxed or otherwise moisture resistant cardboard, the cardboard being folded so that the waxed surface is inside, the liner being so formed that it includes a bottom having multiple layers of cardboard for added safety.

The liner can be an open topped container but in a preferred form is closed for disposal using a lid.

Preferably the liner is in the form of a disposable sharps container having a disposable body, a top section and a lid securable to the top section, the top section having an opening formed therein and being secured to the body, the lid being provided to close the opening and prevent access to the interior of the container. Preferably the disposable container is made from wax or otherwise treated cardboard to improve liquid retention.

The top section and lid are preferably molded or otherwise formed from plastic. The body is typically a cardboard paper or plastic container.

Preferably, the disposable container includes a funnel adjacent the opening. The funnel can be formed as part of the cardboard container or separately thereof in cardboard or plastics material or as above described as part of the reusable container. Alternatively, the funnel can be formed as part of the plastics top section and projecting down into the container. In a most preferred form the funnel and the plastics top section and the cardboard container are usually formed as a single disposable unit.

The plastics top section is typically a flat panel clipped in place in the cardboard body and being biased against removal once clipped in place. The opening from the mouth is typically circular, although other shapes can be used.

The lid is typically biased against removal once in place and is preferably circular, having a plurality of resilient lugs including shoulders adapted to lock the lid to the top section. The plastics top section and the lid preferably include sealing means to seal the container against egress of fluids. The seals are typically O-ring seals or resilient rubber sealing members secured to the top section at its point of engagement to the cardboard container. In the case of the lid, an O-ring seal is typically used.

In another embodiment the lid includes an annular channel sealingly engageable with the top section so that once the lid is in place the annular channel seals and prevents removal of the lid.

In another embodiment the disposable container is held inside an outer liquid proof layer which is typically a flexible plastics bag. The plastics bag is preferably stored flat and is expandable.

The container is typically used with a number of accessories including a support platform, the container body having support platform locating means so the container can be positioned over an opening in the support platform so that when the openable closure is released, the liner can free fall through the opening in the support platform and into a waste container.

The container body also preferably includes a handle so that the base can be safely handled without an operator placing his hands near the mouth of the container body. Typically, the container body includes an open bottom, the openable closure means being a trap door in the bottom, the container body have an upstanding side wall and the handle being located in or on the side wall.

BRIEF DESCRIPTION OF THE DRAWINGS

In order that the invention can be more readily understood and be put into practical effect, reference will now be made to the accompanying drawings which illustrate preferred embodiments of the invention and wherein.

METHOD OF PERFORMANCE

Figure 1:
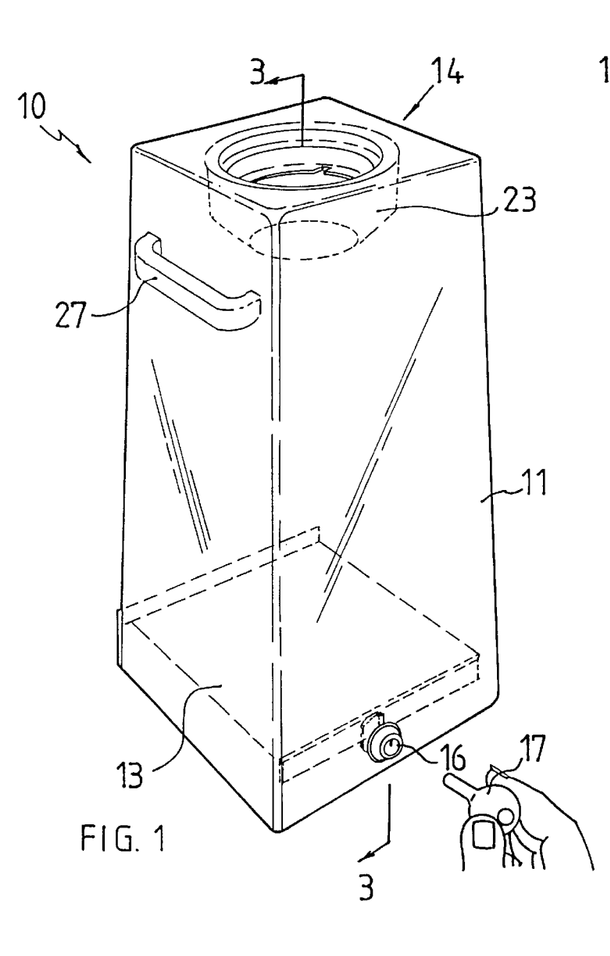
FIG. 1 is a perspective view from one side illustrating a reusable sharps container according to the present invention.
Figure 2:
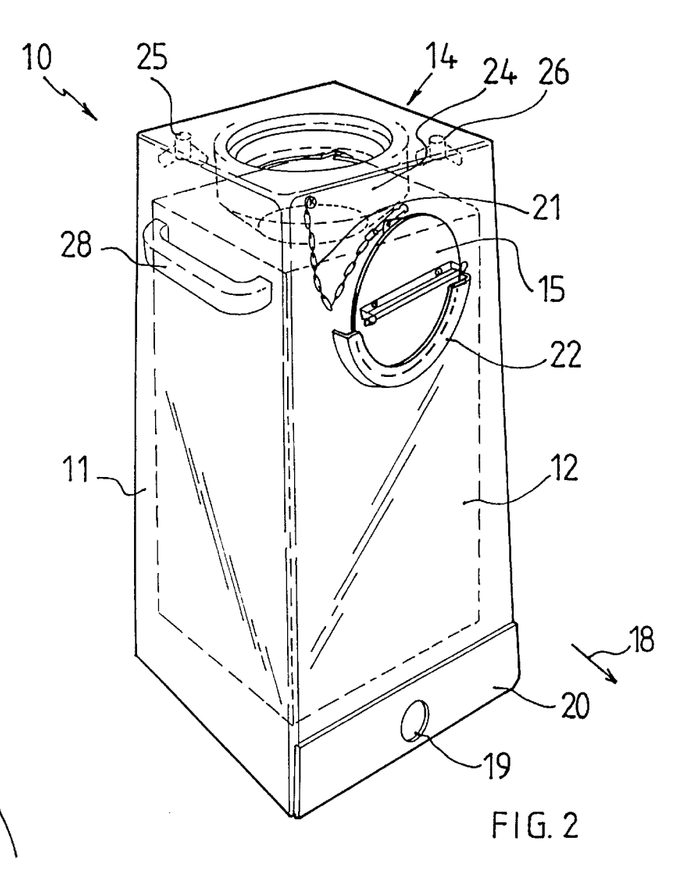
FIG. 2 is a perspective view illustrating the container of FIG. 1 from the opposite side.

Referring to the drawings and initially to FIGS. 1 and 2, there is illustrated a reusable sharps container 10 comprising a hollow outer container body 11, a disposable liner 12 (shown in phantom in FIG. 2) located inside the hollow body, the hollow body having a slidable trap door (shown in phantom in FIG. 1) 13 which can be removed so that the liner 12 can be replaced and the container having a mouth 14 with a co-operating lid 15 so that sharps can pass through the opening 14 and into the liner 12.

The container body in the illustrated embodiment is made from plastic material and in this case is approximately 200 mm wide with an 80 mm at 14.

The trap door 13 is locked using a lock 16 which can be operated by a key 17 to release the trap door so that it can be slid in the direction of the arrow 18 by a user locating his finger in the aperture 19 of the flange 20 and withdrawing the trap door.

It will be appreciated that when the trap door is withdrawn, the liner 12 will free fall out of the container.

A new liner can be inserted into the container and the trap door 13 slid back into position and locked.

The lid 15 is secured to the container using a chain 21 and as shown in FIG. 2, the lid 15 is retained in a cradle 22 when not in use, but can be removed from the cradle 22 and pushed into the mouth 14 to close the container once the liner 12 is full. In the embodiment of FIG. 1, the mouth 14 includes a projecting portion in the form of a funnel 23 which in this case is molded integrally with the container body. In the FIG. 2 embodiment, a funnel 24 is employed which is removable for cleaning purposes using wingnuts 25 and 26. Handles 27 and 28 are employed so that the container can be handled by the user without having to touch the region around the mouth 14.

Figure 3:
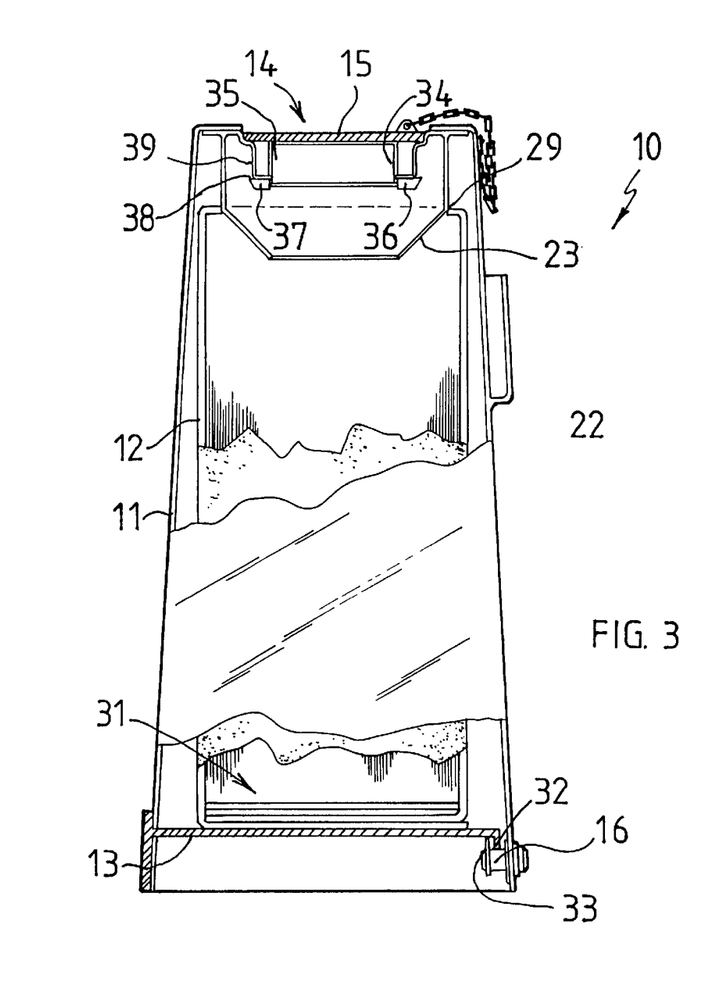
FIG. 3 is a section through 3—3 of FIG. 1.

Referring now to FIG. 3, the container 10 is illustrated in section and in this case, the lid 15 is shown locked in place over the mouth 14 and the funnel 23 is shown protruding into the liner 12. It will be appreciated that the liner 12 is securely located in position inside the container body 11 by virtue of the funnel 23 and the size of the opening 29 of the liner 12. In addition, the tapered wall of the container is either very close to the upper corners 30 of the liner, or the liner is wedged in place so that this further minimises the chance of the liner 12 moving when located in position as shown.

The liner 12 in this embodiment is made from a plastic lined or wax lined cardboard container folded from a blank of cardboard material so that the bottom 31 of the container is folded into multiple layers as shown. This enables the container to effectively absorb any small amounts of liquids into the cardboard in the lower portion of the container and also reduces the likelihood of the bottom of the container being punctured by sharps.

As can been seen in FIG. 3, the trap door 13 includes a flange 32 engageable with a tongue 33 of the lock 16 and supports the liner in its position as illustrated in FIG. 3.

Figure 4:
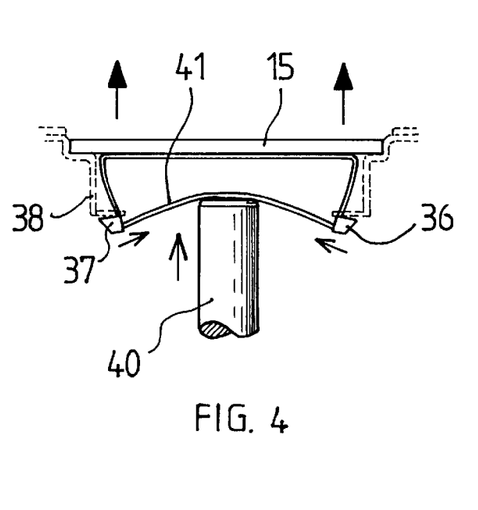
FIG. 4 is a section through a typical lid showing how the lid is released.

The lid 15 includes spring steel or plastics flanges 34 and 35 supporting latches 36 and 37 respectively which slide along the walls of a neck portion 37 of the mouth and catch behind shoulders 38. The lid can only be released from inside the container body and only once the liner has been removed. The method of releasing the lid is illustrated in FIG. 4, where a tool 40 is pushed up into the container from the inside to engage a release strap 41 to thereby retract the catches 36 and 37 and release the lid 15.

Figure 5:
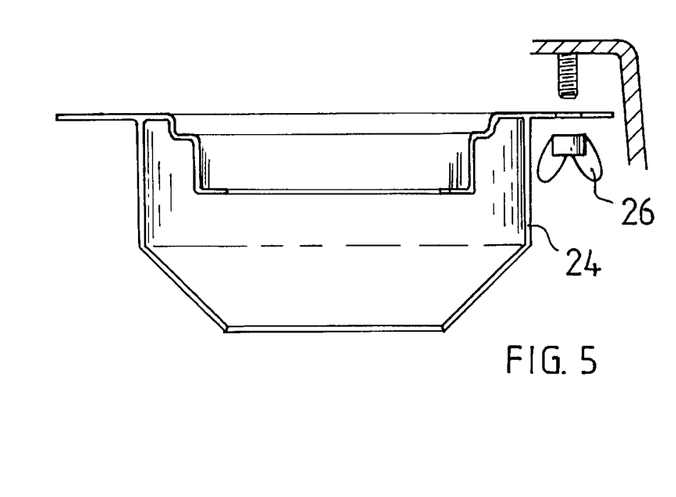
FIG. 5 is a section showing one embodiment of a detachable protruding portion of a mouth suitable for a container according to the present invention.

Referring now to FIG. 5, there is illustrated a removable funnel 24 showing that the funnel can be removed for cleaning purposes so that only those portions which might come in contact with biological materials need be cleaned.

It will be appreciated in the illustrated embodiment that the liner is disposed of and only the funnel section would normally be exposed to pathological material contained on the sharps entering the container and therefore the funnel 24 need only be subjected to sterilization procedures.

Figure 6:
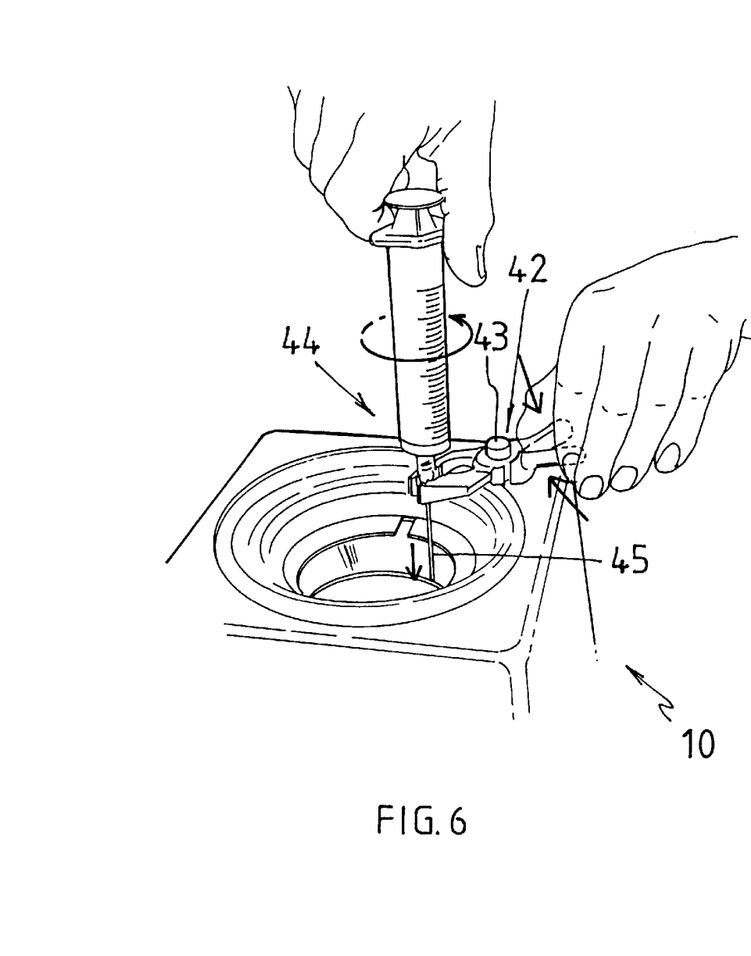
FIGS. 6 and 7 are pictorial views illustrating two applications of the present invention.
Figure 7:
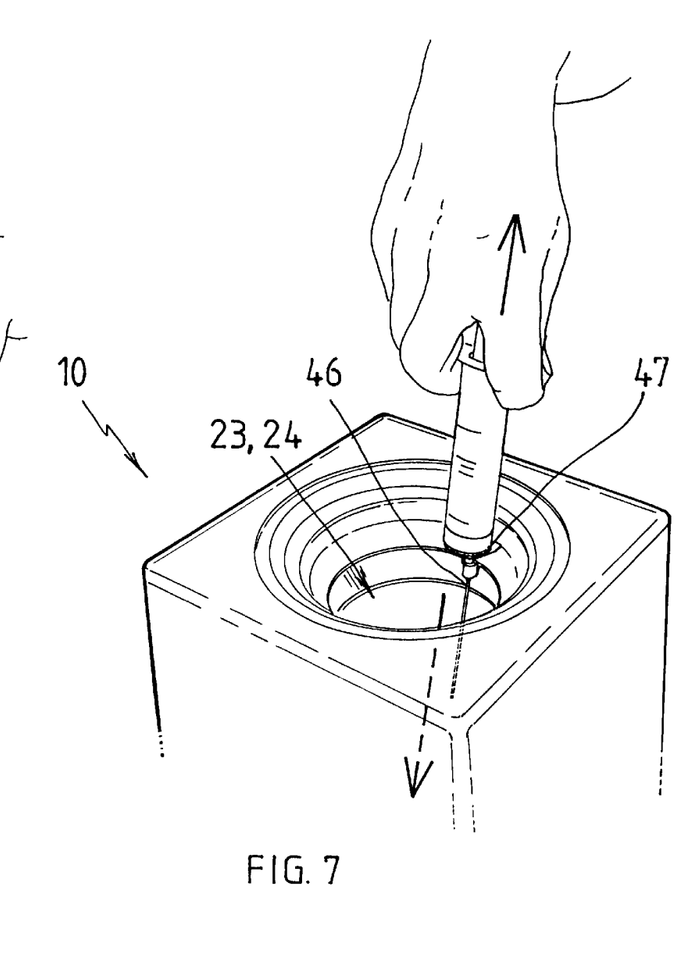

Referring now to FIGS. 6 and 7, there is illustrated application of the present invention to removal of needles from hypodermic syringes. In FIG. 6, the container is equipped with a small pair of miniature pliers 42 pivotally mounted to the container 10 at 43 so that the lure lock syringe 44 can have its hypodermic needle 45 removed and will automatically drop into the container. In the case of the syringe where the hypodermic needle is frictionally held in place, there is in the case of the hypodermic needle 46 of FIG. 7, a notch 47 is provided in the neck of the funnel 23, 24 so that the needle can be automatically detached and fall into the container.

Figure 8:
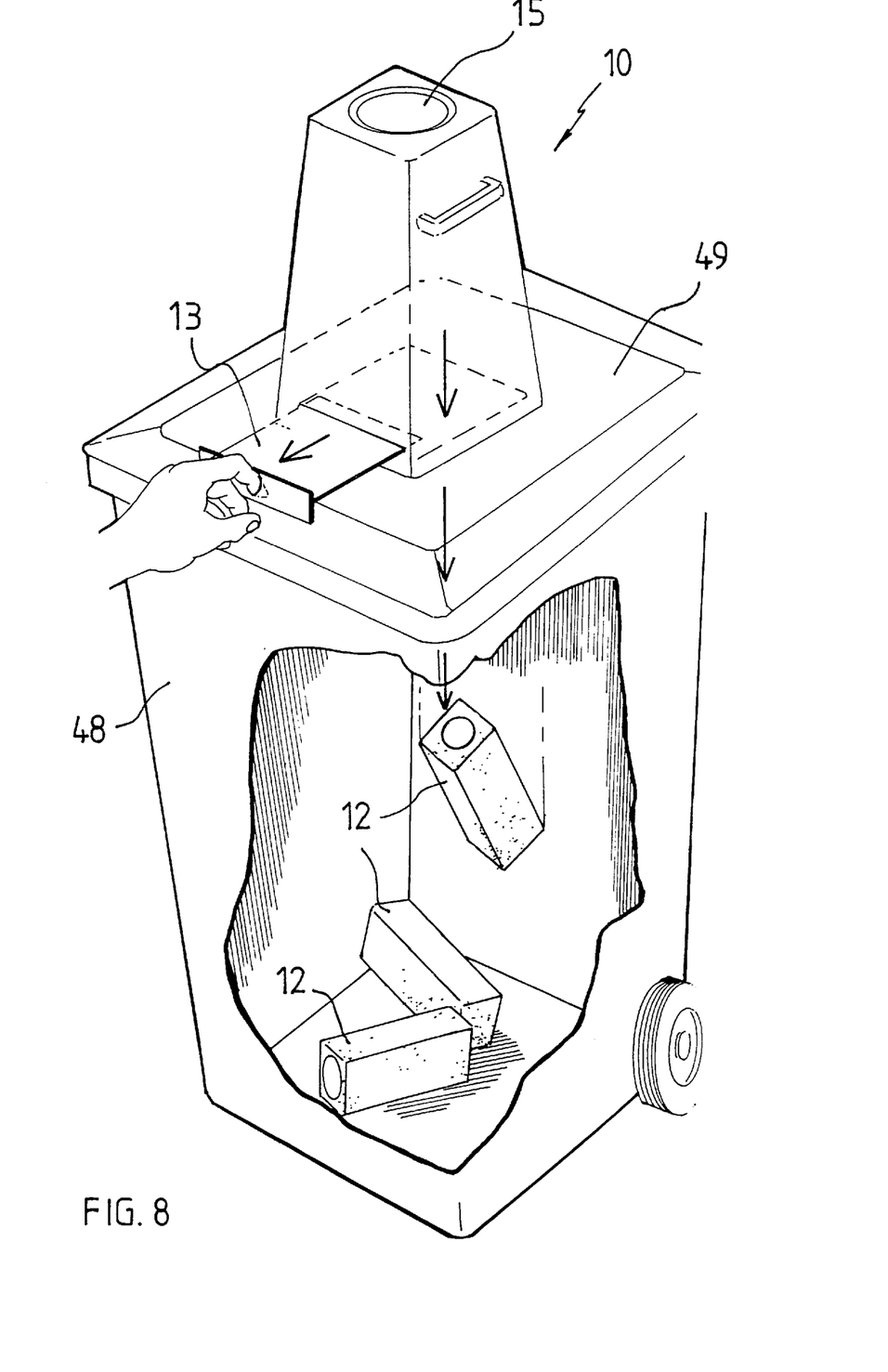
FIG. 8 is a cut-away perspective view illustrating use of the container with a support platform and waste container.

Referring now to FIG. 8, there is illustrated a method of disposing of full liners 12 into a waste container 48, and in this case a support platform 49 is provided with an opening and a container 10 with lid 15 in place, this is simply positioned over the opening and the trap door 13 retracted so that the liner free falls into the waste container 48.

It will be appreciated that in the disposal technique, the liners 12 can be simply and conveniently discharged from the container 10.

Once the liner has been discharged, the tool 40, according to FIG. 4, can be inserted up into the inside of the container 10 to release the lid 15. The new liner can then be located in place, the trap door 13 locked in the closed position and the container is ready for reuse.

If it is desirable to sterilize the funnel, the embodiment of FIG. 5 can be employed where the funnel 24 can be removed before the liner is put in place and substituted with a clean funnel, the contaminated funnel can be sent for sterilization. In this embodiment, two funnels would be provided with each container so that the container is not out of use while the funnel is being sterilized.

As an alternative the funnel can be produced as part of the liner and disposed of with the liner. Likewise the lid can be disposed of with the liner. This is described below.

Figure 9:
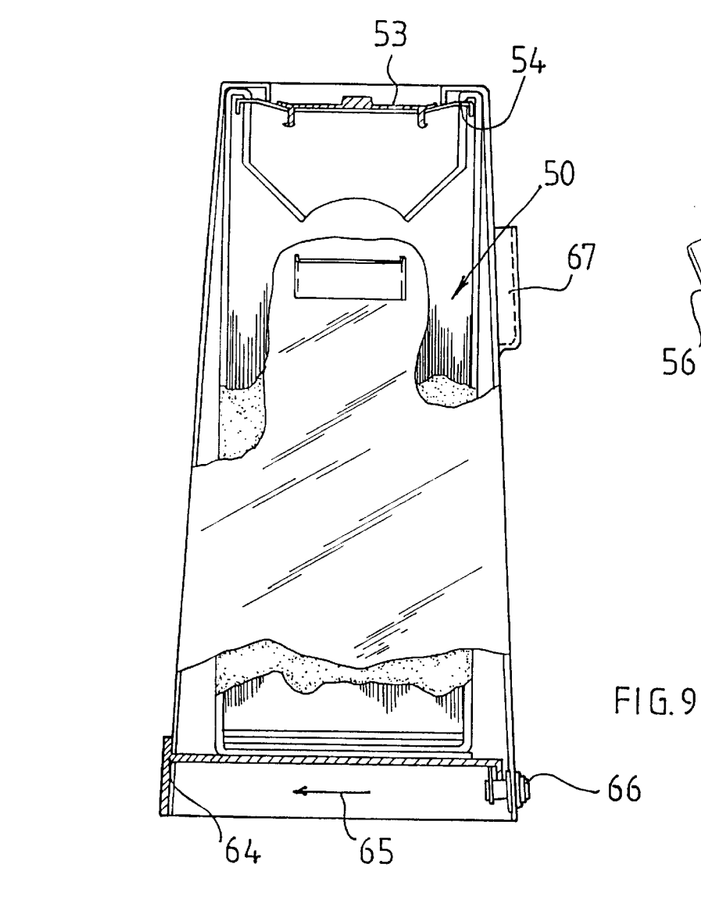
FIG. 9 is a perspective view illustrating a typical disposable container suitable for use as a liner and showing its top section prior to being assembled with the cardboard body.

Referring to FIG. 9, there is illustrated a disposable container 50 comprising a folded cardboard body 51, a top section 52 made from plastic material and a lid 53 (see FIG. 10) which when assembled, form a sealed container for medical sharps. As can be seen in FIG. 9, the plastic top section 52 comprises a panel 54 having an opening 55, lug 56 and side flanges 57. The lug 56 can be manually fitted into slots 58 in the cardboard box 51 as can be seen in FIG. 10, when so fitted, the panel 54 is flexibly distorted so that it is biased as shown and cannot be readily removed from the box 51.

The panel 54 preferably includes a resilient seal fitted around the marginal edge of the panel 54 in known fashion to provide a seal between the panel 54 and the container 51. The seal is not illustrated in the drawings. The panel includes notches 59 to assist in removing hypodermic needles from syringes.

Figure 10:
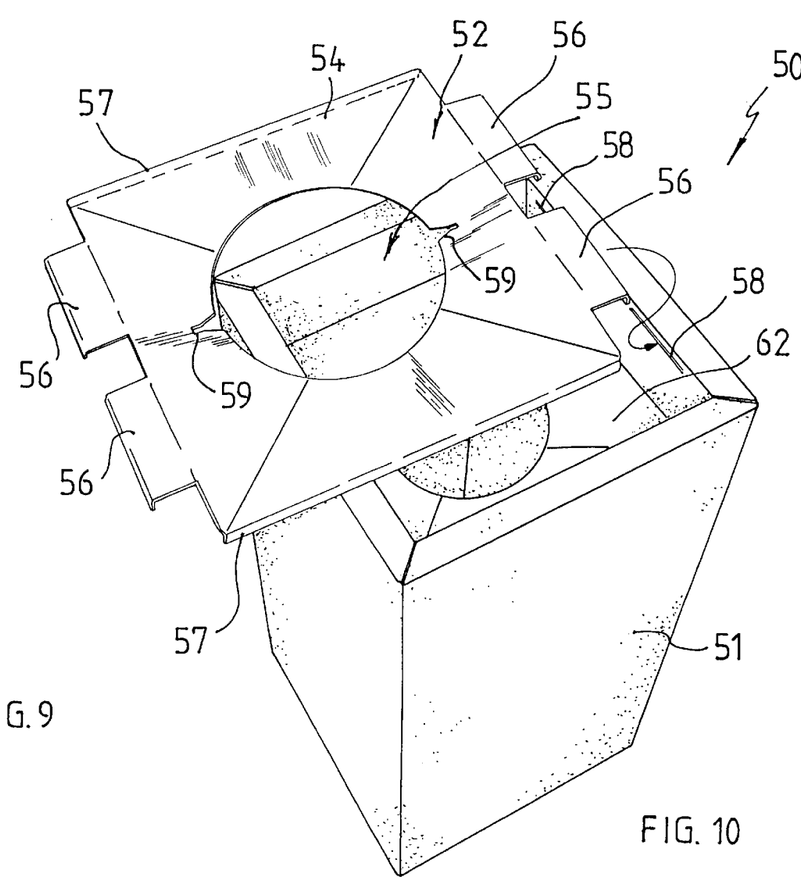
FIG. 10 is a cut-away side view of the container of FIG. 9 shown operatively positioned within a reusable external container.

Referring now to FIG. 10, there is illustrated the container 50 inside a reusable container 61 of the type described above in FIG. 1 although there are some differences.

A comparison of the two containers shows that the funnel 62 previously formed as part of the container is now formed as part of the disposable cardboard container or liner and the lid 53 also previously formed as part of the reusable container is now formed as a disposable portion. The lid 53 includes lugs 63 located at spaced intervals about the lid 53 so that once the lid 53 is in place, the lugs inhibit removal.

The funnel 62 serves the purpose of providing a level indicator of sharps within the container and thereby an indicator as to when it is time to dispose of the container. The funnel 62 allows a user to inspect the level of the sharps from a position externally of the liner of the container.

The funnel 62 indicates that replacement of the container is to take place when the level of the sharps within the container is close to or at the inner end of the funnel. The same indication is also provided by the funnels 23,24 described earlier.

A user first puts the lid 53 in place and then removes the drawer 64 in the direction of the arrow 65 after unlocking the barrel lock 66 so that the container 50 freefalls into a pathogenic waste container. The reusable container 61 is equipped with a pocket 67 in which the lid 53 can be stored while the container is being filled.

Figure 11:
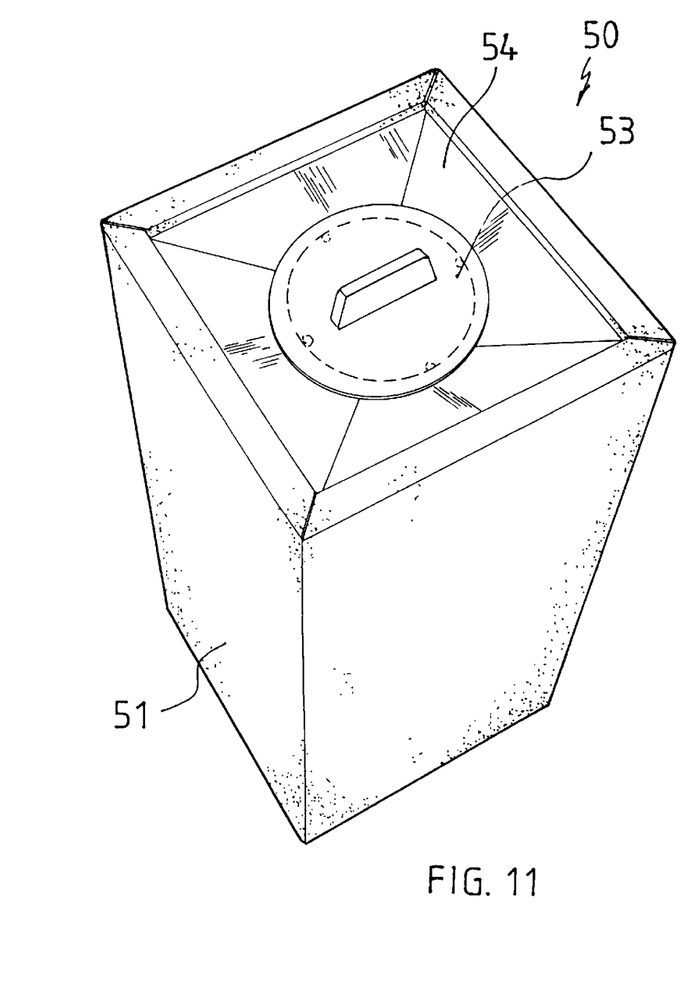
FIG. 11 is a perspective view showing the disposable container ready for disposal.
Figure 12:
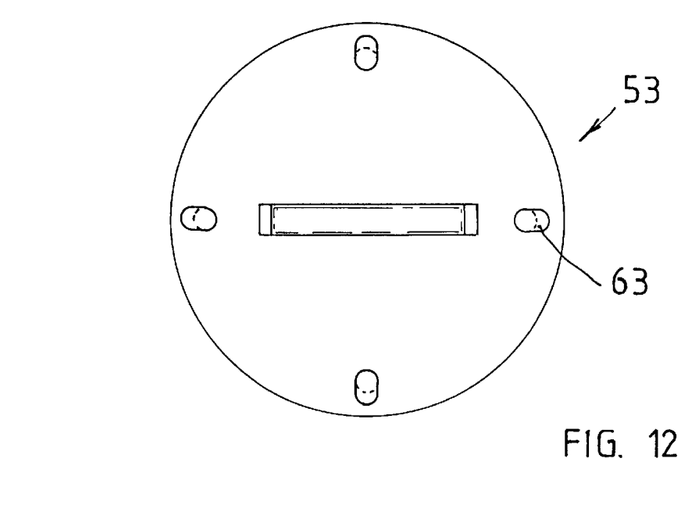
FIGS. 12 and 13 are plan and cut-away side views of a typical lid.

Referring now to FIGS. 11 and 12, there is shown fully assembled container 50 is illustrated in FIG. 11 and where appropriate, like numerals have been used to illustrate like features.

Figure 13:
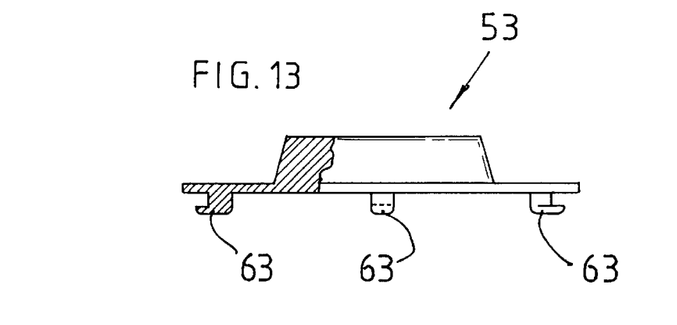

FIGS. 12 and 13 illustrates the lid 53.

Figure 14:
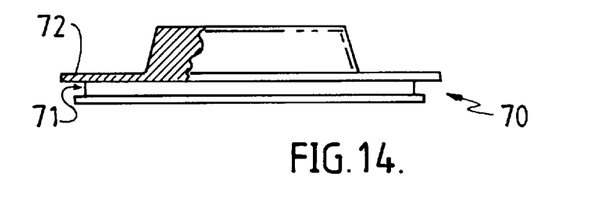
FIGS. 14 and 15 are plan and cut-away side views of an alternative lid.
Figures 15, 16:
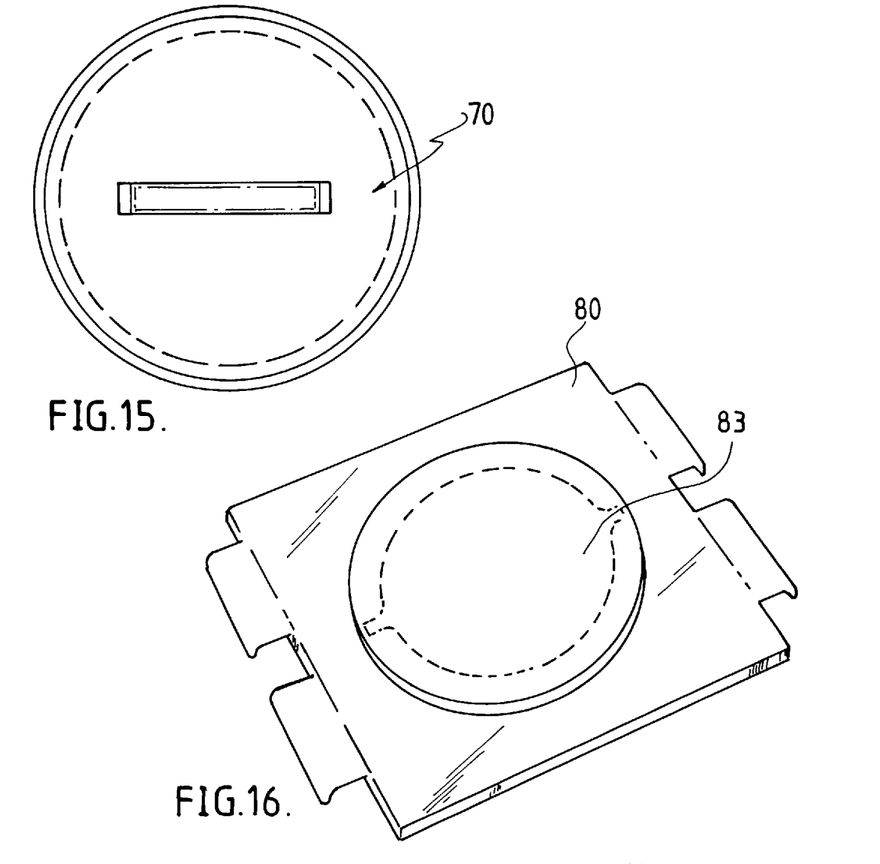
FIGS. 16 and 17 are views illustrating another embodiment of a lid and its associated top section.

FIGS. 14 and 15 illustrate an alternative lid 70 in this case employing a polyethylene or equivalent plastic having an annular channel dimensioned slightly less than the thickness of the top section 62 so that a seal is obtained without the need for an O-ring. The lip 72 overhangs slightly and is sufficiently thin and narrow to resist tampering.

Figure 17:
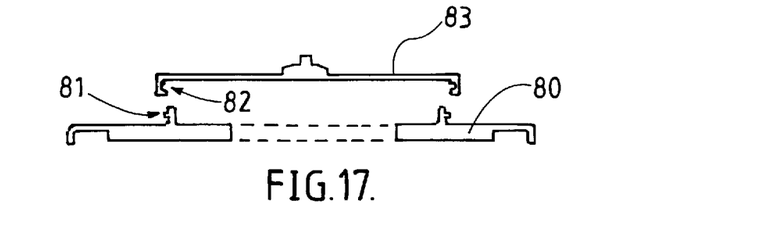

Referring to FIGS. 16 and 17 there is illustrated another embodiment of the invention in this case employing a top section 80 having an annular projection 81 co-operating with an annular channel 82 of a lid 83. The lid and projection have co-operating shoulders which lock the lid in place against removal and bring about an effect seal.

Figure 18:
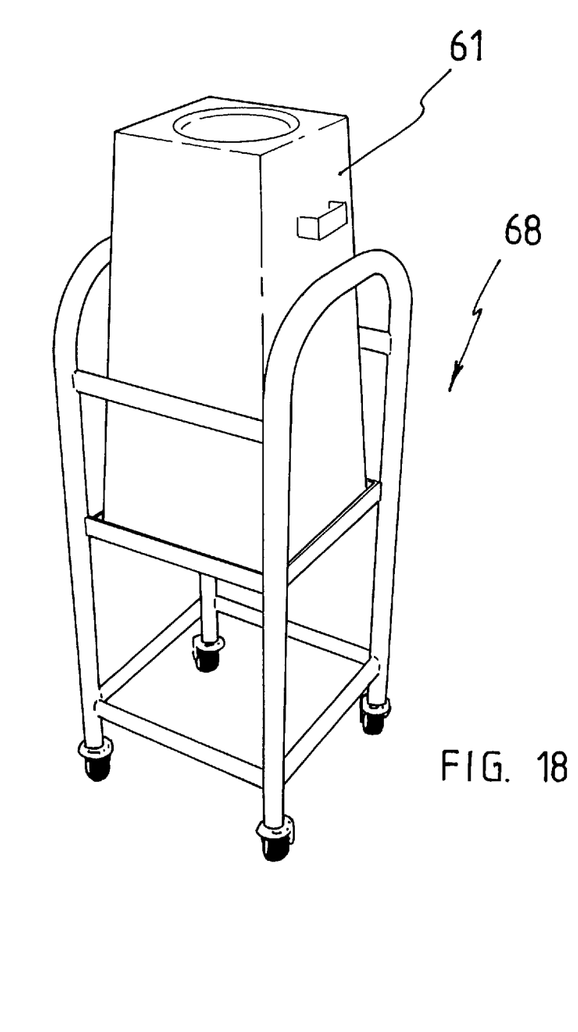
FIGS. 18 and 19 are drawings illustrating application of the teachings of the present invention to a clinical situation.
Figure 19:
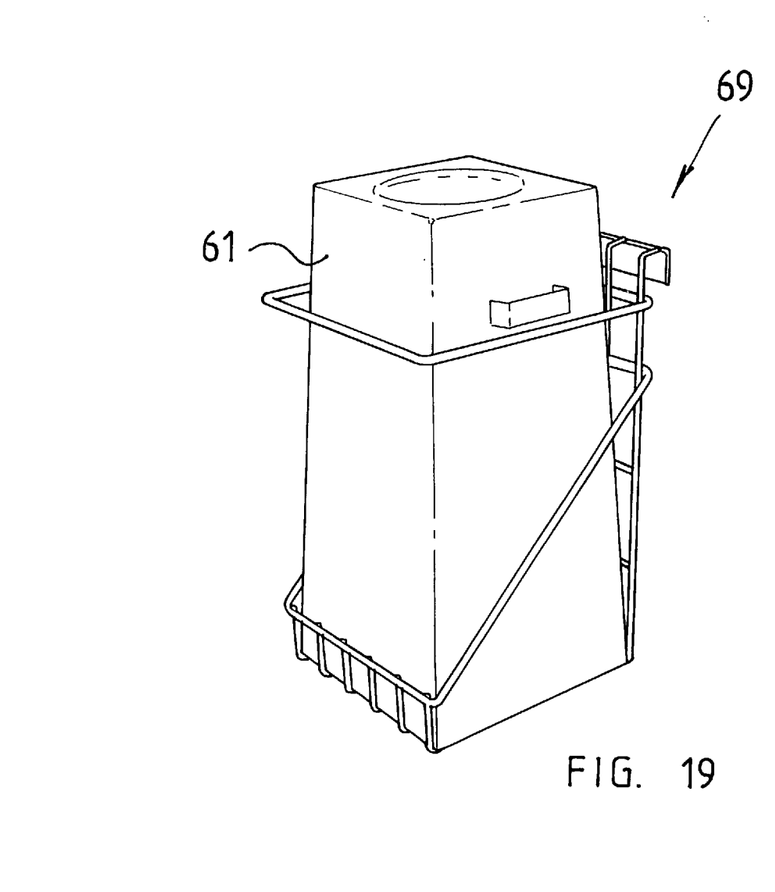

FIGS. 18 and 19 illustrate a trolley arrangement 68 and storage rack 69 respectively as being two typical ways in which the container 61 can be positioned for use in a clinical environment.

Figure 20:
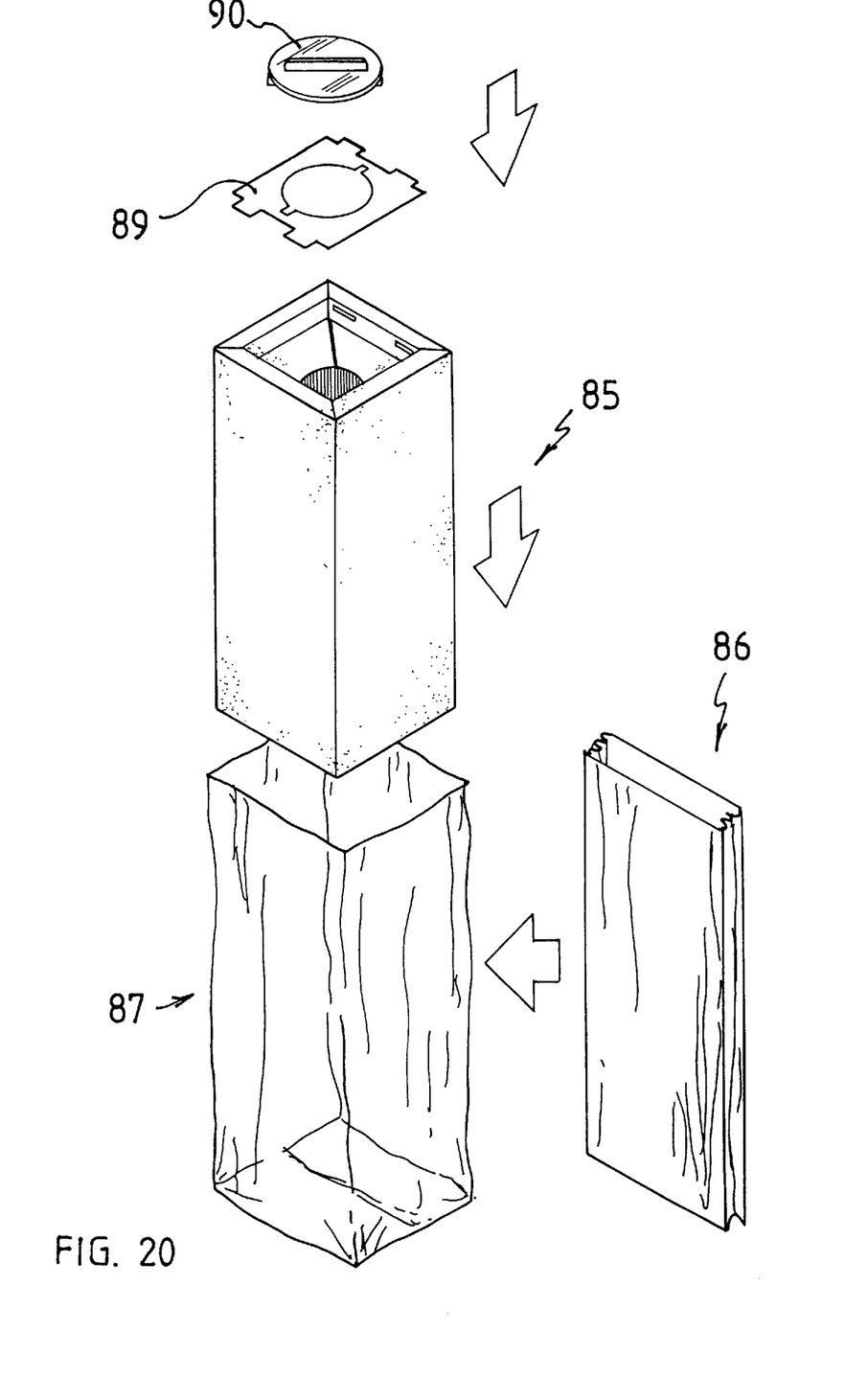
FIG. 20 is an assembly diagram illustrating a disposable sharps container according to another embodiment of the invention.

Referring to FIG. 20 there is illustrated another embodiment of a disposable shapes container that can be used on its own or preferably as a liner for a reusable container. In this case there is provided a container 85 similar to the container 50 illustrated in FIG. 9. The container is used in combination with a plastics bag the plastics bag being shown in its folded state at 86 and then expanded at 87. The cardboard container 85 goes into the bag, the upper edges of the bag fold into the funnel 88 and then the top section 89 which operates in the same way as top section 52 (see FIG. 9) clips in place to hold the plastic bag secure. A lid 90 in this case fits as a bayonet fit although lids of the type previously described can be used.

Figure 21:
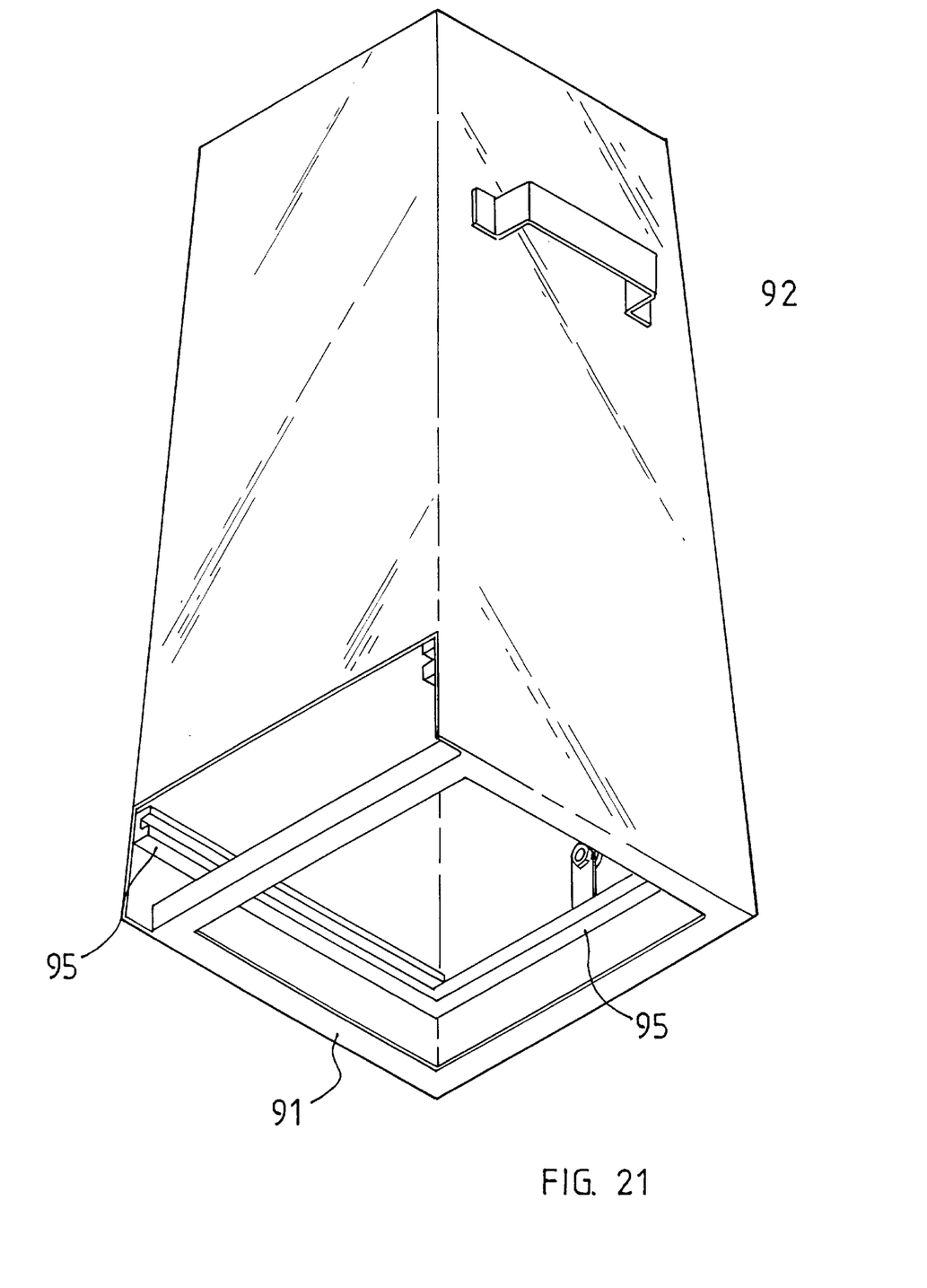
FIG. 21 is a view of another form of reusable container.
Figure 23:
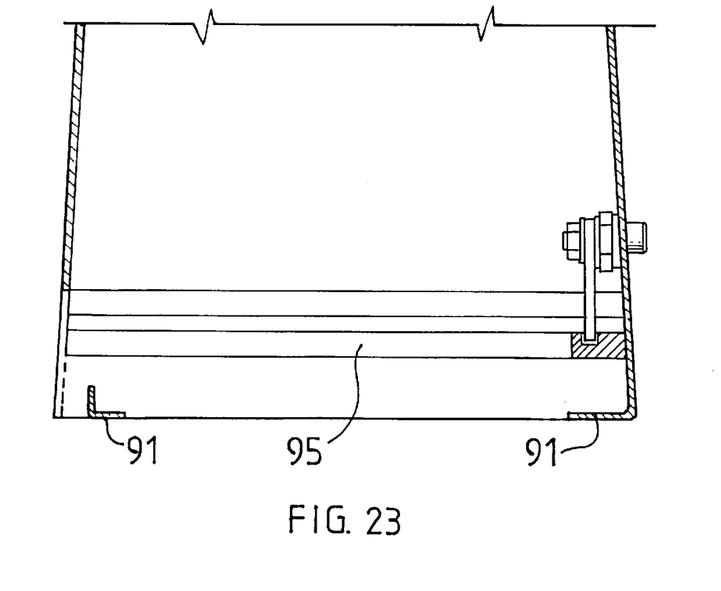
FIG. 23 is a section through part of the container of FIG. 21.

FIG. 21 and 23 illustrates a form of square bracing using a flange 91 of the bottom of a reusable container 92 so that the bottom does not flex and potentiate accidental dislodgment of the drawer.

Figure 22:
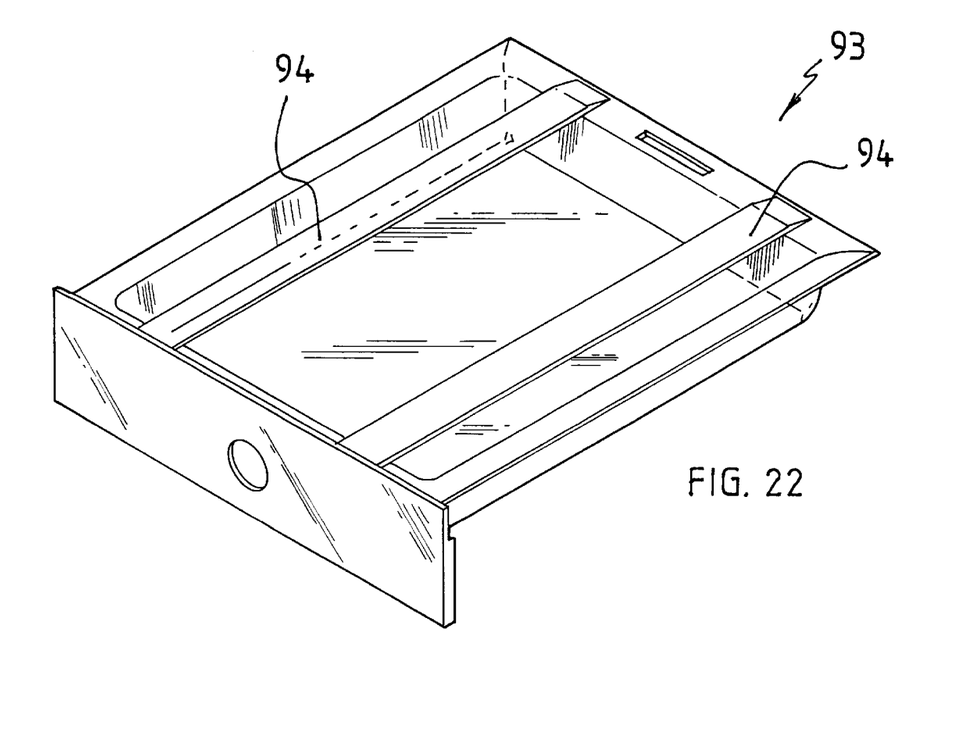
FIG. 22 is a perspective view illustrating another embodiment of a removable base.

A typical drawer 93 is shown in FIG. 22 wherein this case the drawer is dished with skid bars 94 on which the disposable container sits. The drawer slides into a framed guide slot 95 (see FIGS. 21 and 23) and this provides an added seal right around the base so that from beneath the container is fully closed.

Whilst the above has been given by way of illustrative example of the present invention, many variations and modifications thereto will be apparent to those skilled in the art without departing from the broad ambit and scope of the invention as set forth in the following claims.

What is claimed is:

1. A sharps container comprising in combination a hollow reusable outer container body and a disposable liner located inside the hollow outer container body to hold sharps, the outer container body having a thin wall, an open base and an openable closure means comprising a trap door which is normally located in a closed position for closing the open base and is moveable to an open position so that the liner can be replaced, and the combination having a mouth and a co-operating lid so that sharps can pass through the mouth and travel into the liner, the lid being used to close the mouth prior to disposal of the liner, the openable closure means being fitted to the outer container body below the liner so that when the trap door is moved to the open position the liner is automatically discharged from the container, the open base being braced about its lower periphery to inhibit flexing of the outer wall adjacent the trap door.

2. A sharps container according to claim 1 wherein the lid is secured to the outer container body.

3. A sharps container according to claim 1 wherein the lid is secured to the liner.

4. A sharps container according to claim 3 wherein the liner comprises a disposable container having a liner body and a separate top section secured to the liner body, the top section having an opening forming the mouth to which the lid is secured.

5. A sharps container according to claim 1, wherein the trap door is a lockable drawer located in a lower base portion of the container.

6. A sharps container according to claim 1 wherein the container body and the liner are generally upright and relatively narrow elongated containers adapted to hold relatively long disposable surgical devices.

7. A sharps container according to claim 1, wherein the container includes a level indicator comprising a funnel projecting into said liner, the funnel providing an external visual indication of the level of sharps in the liner.

8. A sharps container according to claim 7 wherein the funnel is formed as part of the liner.

9. A sharps container according to claim 1 wherein the liner comprises a container located inside a liquid impervious outer container.

10. A sharps container according to claim 9 wherein the liner includes a bottom section and a top section clipped into the bottom section, the top section having an opening forming said mouth and serving to retain said outer container operatively secured to the bottom section.

11. A sharps container according to claim 1, wherein the outer container further comprises a supporting frame extending around the open base and co-operating with the trap door so that when the trap door is in the closed position it engages the supporting frame to close a periphery of the open base.

12. A sharps container according to claim 1, wherein the liner comprises a container body and a top section securable to the liner container body, the lid being securable to the top section, the top section having an opening, the month being defined by the opening, and the lid being provided to close the top section and inhibit access to the interior of the liner body.

13. A sharps container according to claim 12 wherein the lid includes a resilient locking means biasing the lid against removal once the lid is used to close the top section.

14. A sharps container according to claim 12, wherein the liner body is substantially box shaped and has a thickened base.

15. A sharps container according to claim 12, wherein the liner is substantially box shaped and includes an outer liquid impervious layer.

16. A sharps container according to claim 12 wherein the liner container body includes a level indicator projecting downwardly from the top section and into the liner body.

17. A sharps container comprising in combination:

a hollow outer container body; and a disposable liner located inside the hollow outer container body to hold sharps, said hollow outer container body further comprising a bottom closure means located below said disposable liner, said bottom closure means having a closed position and an open position so that in the closed position said disposable liner remains within said hollow outer container and so that in the open position said disposable liner is automatically discharged through said bottom closure means, the combination having a mouth and a co-operating lid so that sharps can pass through the mouth and travel into the liner, wherein the lid is used to close the mouth during disposal of the liner.

* * * * *